US012778686B2

(12) United States Patent
Hyde et al.

(10) Patent No.: US 12,778,686 B2
(45) Date of Patent: Nov. 3, 2026

(54) AUTOMATED METHOD FOR DETERMINING THE SAFETY OF A STEREOTACTIC SURGICAL TRAJECTORY

(71) Applicant: ClearPoint Neuro, Inc., Solana Beach, CA (US)

(72) Inventors: Damon Hyde, Somerville, MA (US); Chen Li, Plainfield, OH (US); Lyubomir Zagorchev, Burlington, MA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 466 days.

(21) Appl. No.: 17/965,631

(22) Filed: Oct. 13, 2022

(65) Prior Publication Data

US 2024/0122657 A1 Apr. 18, 2024

(51) Int. Cl.

| | |
|---|---|
| ***A61B 34/00*** | (2016.01) |
| ***A61B 34/10*** | (2016.01) |
| ***A61B 90/00*** | (2016.01) |
| ***G06T 17/20*** | (2006.01) |

(52) U.S. Cl.

CPC .............. *A61B 34/25* (2016.02); *A61B 34/10* (2016.02); *A61B 90/36* (2016.02); *G06T 17/20* (2013.01); *A61B 2034/105* (2016.02); *A61B 2034/107* (2016.02); *A61B 2090/367* (2016.02)

(58) Field of Classification Search

None

See application file for complete search history.

(56) References Cited

U.S. PATENT DOCUMENTS

| | | | | |
|---|---|---|---|---|
| 7,616,794 | B2 * | 11/2009 | Moeller | G06T 7/11 382/128 |
| 2016/0155232 | A1 * | 6/2016 | Sela | G16H 20/40 382/103 |
| 2021/0110605 | A1 * | 4/2021 | Haslam | G06T 7/11 |
| 2021/0343397 | A1 * | 11/2021 | Orr | G16H 30/20 |
| 2022/0108525 | A1 * | 4/2022 | Zagorchev | A61B 5/291 |
| 2022/0336097 | A1 * | 10/2022 | Shelton, IV | G06T 11/00 |

* cited by examiner

*Primary Examiner* — Shahdeep Mohammed

(74) *Attorney, Agent, or Firm* — Sheppard Mullin Richter & Hampton LLP

(57) ABSTRACT

Systems and methods provide a neurosurgeon with real-time feedback on safety of prospective surgical trajectories, which can simultaneously reduce surgical intervention times and improve patient safety. Examples can determine a level of safety for a prospective surgical trajectory by determining a number of times that a prospective surgical trajectory representation (e.g., a 1D line representing a prospective surgical trajectory) intersects (a) a patient-specific 3D cortical surface representation (i.e., a 3D representation representing an exterior surface of the patient's brain cortex); and (b) one or more patient-specific 3D hazard brain region representations (e.g., 3D representations representing hazard brain regions of the patient to be avoided during surgery).

20 Claims, 9 Drawing Sheets

100

100

AUTOMATED METHOD FOR DETERMINING THE SAFETY OF A STEREOTACTIC SURGICAL TRAJECTORY

TECHNICAL FIELD

The present disclosure relates generally to medical technologies, and more particularly, some examples relate to determining a level of safety for a prospective stereotactic surgical trajectory.

BACKGROUND

The brain cortex is the outer layer of neural tissue of the human brain. The brain cortex is comprised of a series of ridges called gyri, and fissures/grooves called sulci. Accordingly, the surface of the human brain (i.e., the "cortical surface") can be highly rugged/irregular. The major blood vessels of the brain lie at the cortical surface and within the sulci.

BRIEF DESCRIPTION OF THE DRAWINGS

The present disclosure, in accordance with one or more various examples, is described in detail with reference to the following figures. The figures are provided for purposes of illustration only and merely depict examples.

Figure 1:
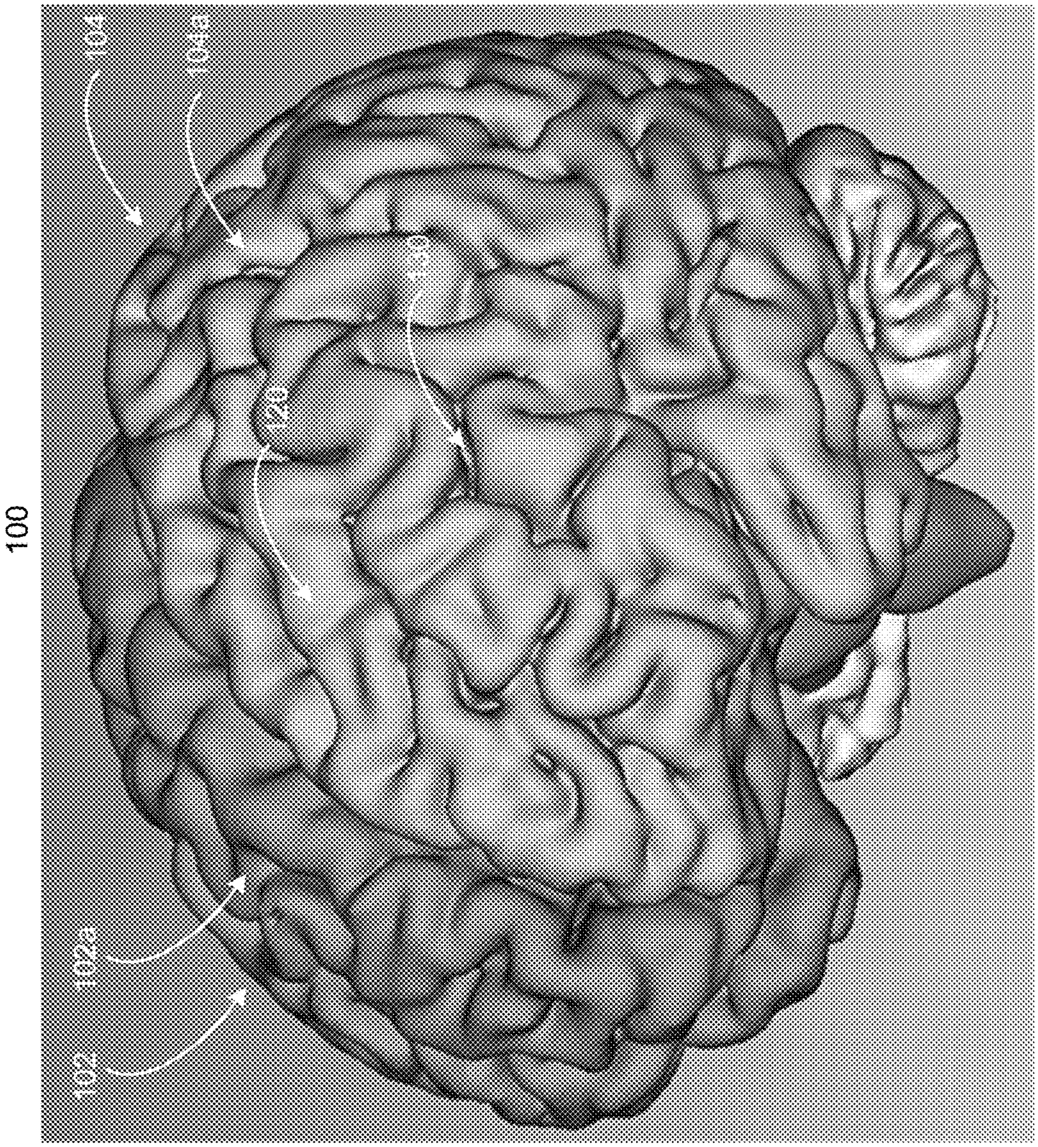
FIG. 1 depicts an example patient-specific brain representation including 3D segments representing cortical hemispheres, in accordance with various examples of the presently disclosed technology.

The figures are not exhaustive and do not limit the present disclosure to the precise form disclosed.

DETAILED DESCRIPTION

Neurosurgeons generally try to evaluate a level of safety for a prospective surgical trajectory before advancing a surgical instrument into/through a patient's brain along the prospective surgical trajectory. Such "pre-advancement trajectory evaluation" can reduce patient trauma by identifying (and then avoiding) unsafe surgical trajectories prior to surgical insertion/advancement.

One way to evaluate a level of safety for a prospective surgical trajectory is to estimate a number of times a surgical instrument advanced along the prospective surgical trajectory would pierce the cortical surface (or relatedly, estimating how closely the surgical instrument advanced along the prospective surgical trajectory would pass to various segments of the rugged/irregular cortical surface). Such an estimation can be a useful safety evaluation tool because the major blood vessels of the brain are primarily located at the cortical surface, and piercing blood vessels of the brain can cause significant patient trauma such as intercranial hemorrhaging. Accordingly, a level of safety for a prospective surgical trajectory can be maximized/improved by minimizing a number of times a surgical instrument advanced along the prospective surgical trajectory would pierce the cortical surface (thereby reducing the likelihood that the surgical instrument would pierce a blood vessel). However, estimating a number of times a surgical instrument advanced along a prospective surgical trajectory would pierce the cortical surface can be challenging due to the highly rugged/irregular nature of the cortical surface.

Relatedly, pre-advancement trajectory evaluation for brain surgeries remains a significant challenge due to reliance on manual and inexact evaluation techniques. In particular, neurosurgeons still largely rely on manual review of a series of images of a patient's brain (e.g., MR or CT images of the patient's brain) resliced orthogonal to a prospective surgical trajectory. Such manual review can be time consuming, and can cause significant delays for complicated interventions that require multiple inter-operative adjustments. These delays can be especially harmful in interventions conducted under computerized tomography (CT) guidance because longer procedures expose the patient to additional radiation.

The current manual approach to pre-advancement trajectory evaluation for brain surgeries also depends heavily on the expertise and judgment of an administering neurosurgeon—which presents drawbacks. In general, human decision-making can take longer than computer/automated decision-making. Also, where only a few neurosurgeons have the requisite expertise to consistently/accurately evaluate safety for prospective surgical trajectories (as described above, such evaluation requires detailed analysis of multiple images sliced orthogonal to a prospective surgical trajectory)—availability for certain surgical procedures can be limited. Limitations of existing imaging technologies (e.g., MR or CT) can also present challenges. For example, based on a series of resliced MR images alone, it can be difficult for a neurosurgeon to discern/estimate how many times, or to what extent, a prospective surgical trajectory would cause a surgical instrument to pierce the highly irregular/rugged cortical surface, and/or any number of other hazardous brain regions to be avoided during surgery.

Against this backdrop, examples of the presently disclosed technology provide systems and methods for automatically evaluating a level of safety for a prospective surgical trajectory using patient-specific 3D brain representations generated from commonly acquired imaging data of a patient's brain (e.g., MR or CT images of the patient's brain). Accordingly, examples can provide a neurosurgeon with real-time (or approximately real-time) feedback on safety of prospective surgical trajectories, which can simultaneously reduce surgical intervention times (especially for complex interventions requiring multiple inter-operative trajectory adjustments) and improve patient safety. Such automated systems can also reduce reliance on neurophysiological expertise, thereby increasing availability for certain surgical procedures.

In various instances, examples can determine a level of safety for a prospective surgical trajectory by determining a number of times that a prospective surgical trajectory representation (e.g., a 1D line representing a prospective surgical trajectory) intersects (a) a patient-specific 3D cortical surface representation (i.e., a 3D representation representing an exterior surface of the patient's brain cortex); and (b) one or more patient-specific 3D hazard brain region representations (e.g., 3D representations representing hazard brain regions of the patient to be avoided during surgery).

As alluded to above, safety for a surgical trajectory can be improved/maximized by minimizing the number of times a surgical instrument advanced along the surgical trajectory pierces the cortical surface. By minimizing piercings of the cortical surface, the likelihood of piercing major blood vessels of the brain—which are located at the cortical surface—can be reduced. Accordingly, examples can determine a level of safety for a prospective surgical trajectory based on a number of times a prospective surgical trajectory representation (representing the prospective surgical trajectory) intersects a patient-specific 3D cortical surface representation (which as will be described below, may be a 3D boundary surface of a volumetric 3D representation of a patient's brain/brain structure). Here, the number of times the prospective surgical trajectory representation intersects the patient-specific 3D cortical surface representation can serve as an estimate/proxy for a number of times a surgical instrument advanced along the prospective surgical trajectory would pierce the patient's cortical surface.

As described above, examples can also determine a level of safety for a prospective surgical trajectory by determining a number of times that a prospective surgical trajectory representation (representing the prospective surgical trajectory) intersects one or more patient-specific 3D hazard brain region representations. Here, a given patient-specific 3D hazard brain region representation may represent a hazard brain region of the patient to be avoided during surgery (examples of hazard brain regions may include various regions/structures of the patient's brain including blood vessels, sub-cortical structures not targeted for surgery, other regions of the brain, etc.). For example, a first sub-cortical structure within a patient's brain may be targeted for surgery (as will be described below, a prospective surgical trajectory may connect a target point within the first sub-cortical structure, and an initial entry point for entering the patient's brain/cortical surface). However, a second sub-cortical structure located proximate to the first sub-cortical structure may be a hazard brain region to be avoided because piercing the second sub-cortical structure would cause unnecessary patient trauma or surgical complications. Accordingly, examples can determine a level of safety for a prospective surgical trajectory (to the target point within the first sub-cortical structure) by determining a number of times that a prospective surgical trajectory representation (representing the prospective surgical trajectory) intersects a patient-specific 3D representation of the second sub-cortical structure (i.e., the patient-specific 3D hazard brain region representation). As alluded to above, the number of times the prospective surgical trajectory representation intersects the patient-specific 3D representation of the second sub-cortical structure can serve as an estimate/proxy for a number of times a surgical instrument advanced along the prospective surgical trajectory would pierce the second sub-cortical structure (i.e. the hazard brain region of the patient).

Examples can also incorporate safety margins into the above described safety evaluations/determinations. Examples can utilize these surgical safety margins to determine whether prospective surgical trajectories pass within a minimum acceptable distance to a hazard (e.g., the cortical surface or other hazard brain regions). For instance, examples can reduce the size of the patient-specific 3D cortical surface representation (or in some cases, a patient-specific 3D brain structure representation of which the patient-specific 3D cortical surface representation is a 3D boundary surface) and increase the size of patient-specific 3D hazard brain region representations in accordance with a desired safety margin (e.g., the patient-specific 3D cortical surface representation can be inwardly contracted by a distance corresponding to the desired safety margin and the patient-specific 3D hazard brain region representations can be outwardly expanded by a distance corresponding to the desired safety margin). Examples can then determine whether a prospective surgical trajectory passes within a minimum acceptable distance (as defined by the desired safety margin) to a hazard by determining if (and if so, how many times/to what extent) a prospective surgical trajectory representation (representing the prospective surgical trajectory) intersects the safety margin-modified patient-specific 3D cortical surface and the safety margin-modified patient-specific 3D hazard brain region representations. In other cases, examples can (1) compute point-to-surface distances between a prospective surgical trajectory representation and (a) the patient-specific 3D cortical surface representation; and (b) boundary surfaces of the patient-specific 3D hazard brain region representations; and (2) compare the computed distances to threshold safety margin distances—to estimate whether (and/or to what extent) a prospective surgical trajectory passes closer than a minimum acceptable distance to a hazard (e.g., the cortical surface or another hazard brain region).

Upon determining a level of safety for a prospective surgical trajectory, examples can provide a notification (to a neurosurgeon, administering clinician, etc.) based on the determined level of safety for the prospective surgical trajectory. Based on this notification, a neurosurgeon can apply their clinical judgment/expertise as a final level of review prior to advancing a surgical instrument along the prospective surgical trajectory (if the prospective surgical trajectory is determined to be safe) or selecting a new/safer prospective surgical trajectory. By allowing a neurosurgeon to focus their efforts/expertise on final analysis of an automated safety evaluation, examples can significantly reduce intervention times, improve patient safety, and increase access to certain brain surgeries.

As will be described in greater detail below, in various cases the provided notification may comprise a "traffic light" type notification. For example, a green light may indicate a "safe" surgical trajectory that pierces the cortical surface just a single time while avoiding hazard brain regions (and in some cases, not passing within a minimum acceptable distance to hazard brain regions). A yellow light may indicate a "less safe" surgical trajectory that e.g., passes closely to hazard brain regions and/or pierces the surface of the cortical surface multiple times. A red light may indicate a "hazardous" surgical trajectory that e.g., pierces one or more hazard brain regions and/or pierces the cortical surface multiple times. As described above, these notifications can be provided to a neurosurgeon in real-time (or approximately real-time) thereby reducing surgical intervention/planning times and improving patient safety.

FIG. 1 depicts an example patient-specific brain 100 representation including 3D segments representing cortical hemispheres (i.e., patient-specific 3D brain structure representations 102 and 104), in accordance with various examples of the presently disclosed technology. Patient-specific brain representation 100 may be a computerized 3D representation of a patient's brain comprised of individual 3D segments (i.e., sub-representations) representing various structures of the patient's brain (e.g., cortical hemispheres, sub-cortical structures, etc.). Patient-specific brain representation 100 can be based on imaging data (e.g., MR or CT scans) of the patient's brain.

As depicted, patient-specific 3D brain structure representations 102 and 104 are 3D segments of patient-specific brain representation 100—and represent different brain structures of the patient's brain. In particular, patient-specific 3D brain structure representation 102 represents the patient's right cortical hemisphere and patient-specific 3D brain structure representation 104 represents the patient's left cortical hemisphere. Here it may be noted that patient-specific brain representation 100 can also include 3D segments representing sub-cortical structures of the patient's brain which would be located within the patient's right and left cortical hemispheres. Such 3D segments representing the sub-cortical structures of the patient's brain are illustrated in conjunction with FIG. 2.

Each patient-specific 3D brain structure representation may include a patient-specific 3D cortical surface representation. For example, patient-specific 3D brain structure representation 102 includes a patient-specific 3D cortical surface representation 102*a*. Patient-specific 3D cortical surface representation 102*a* is a 3D boundary surface of patient-specific 3D brain structure representation 102 (here it should be understood that patient-specific 3D brain structure representation 102 is a volumetric representation while patient-specific 3D cortical surface representation 102*a* is a 3D surface representation), and represents the cortical surface of the patient's right cortical hemisphere. Likewise, patient-specific 3D brain structure representation 104 includes a patient-specific 3D cortical surface representation 104*a*. Patient-specific 3D cortical surface representation 104*a* is a 3D boundary surface of patient-specific 3D brain structure representation 104, and represents the cortical surface of the patient's left cortical hemisphere.

Examples can generate patient-specific brain representation 100 by adapting a generalized brain representation (i.e., a non-patient-specific representation of the human brain) to patient-specific brain image data commonly acquired in clinical settings (e.g., MR or CT scans of a patient's brain obtained before or during a surgical intervention). In this way, examples of the presently disclosed technology can be easily reproduced across different patients, procedures, sites, etc. Accordingly, examples of the presently disclosed technology may improve upon existing pre-advancement surgical trajectory evaluation methodologies which are not as easily reproducible.

Where patient-specific 3D brain structure representations 102 and 104 are voxel-based representations, examples can generate 3D cortical surface representations 102*a* and 104*a* by applying a marching cubes algorithm to 3D brain structure representations 102 and 104 respectively.

In certain examples, the generalized brain representation described above may comprise a 3D mesh representation. A mesh (or surface mesh) may refer to a representation of a larger domain (e.g., a volume or surface) comprised of smaller discrete cells called mesh elements, and mesh vertices at the junctions of adjacent/adjoining mesh elements. Meshes can be used to compute solutions to equations across individual mesh elements, which then can be used to approximate solutions over the larger domain. For example, meshes can be used to compute volumes contained within 3D closed mesh boundary surfaces.

By adapting a generalized (mesh) brain representation to imaging data of the patients' brain, examples can generate patient-specific (mesh) brain representations. These patient-specific (mesh) brain representations may preserve point-based correspondences between mesh vertices of the generalized 3D (mesh) brain representation and mesh vertices of the patient-specific (mesh) brain representations. These point-based correspondences can be used to identify the various brain structures of the patient's brain, represented by the 3D segments of patient-specific brain representation 100 (e.g., patient-specific 3D brain structure representation 102 representing the patient's right cortical hemisphere and patient-specific 3D brain structure representation 104 representing the patient's left cortical hemisphere).

Referring again to FIG. 1, patient-specific brain representation 100 may comprise a 3D mesh representation. In these examples, the various 3D segments of patient-specific brain representation 100—including patient-specific 3D brain structure representation 102 and patient-specific 3D brain structure representation 104—may be 3D mesh volumes comprised of mesh elements and mesh vertices. Relatedly, 3D cortical surface representations 102*a* and 104*a*—which as described above are 3D boundary surfaces of patient-specific 3D brain structure representations 102 and 104 respectively—may be 3D closed mesh boundary surfaces comprised of mesh elements and mesh vertices.

FIG. 1 can also be useful for visualizing the highly rugged/irregular surface of the brain cortex. As described above, the brain cortex is comprised of a series of ridges called gyri (e.g., gyrus 120), and fissures/grooves called sulci (e.g., sulci 130). Accordingly, the surface of the human brain (i.e., the surface of the brain cortex) can be highly rugged/irregular.

As alluded to above, safety for a surgical trajectory can be improved/maximized by piercing the cortical surface a minimal number of times (e.g., only once) in order to reduce the likelihood of piercing major blood vessels of the brain—which are primarily located at the cortical surface. Accordingly, examples can determine a level of safety for a prospective surgical trajectory based on a number of times a prospective surgical trajectory representation (representing the prospective surgical trajectory) intersects a patient-specific 3D cortical surface representation (e.g., 3D cortical surface representations 102*a* and 104*a*). Here, the number of times the prospective surgical trajectory representation intersects the patient-specific 3D cortical surface representation can serve as an estimate/proxy for a number of times a surgical instrument inserted/advanced along the prospective surgical trajectory would pierce the surface of the patient's brain cortex.

Figure 2:
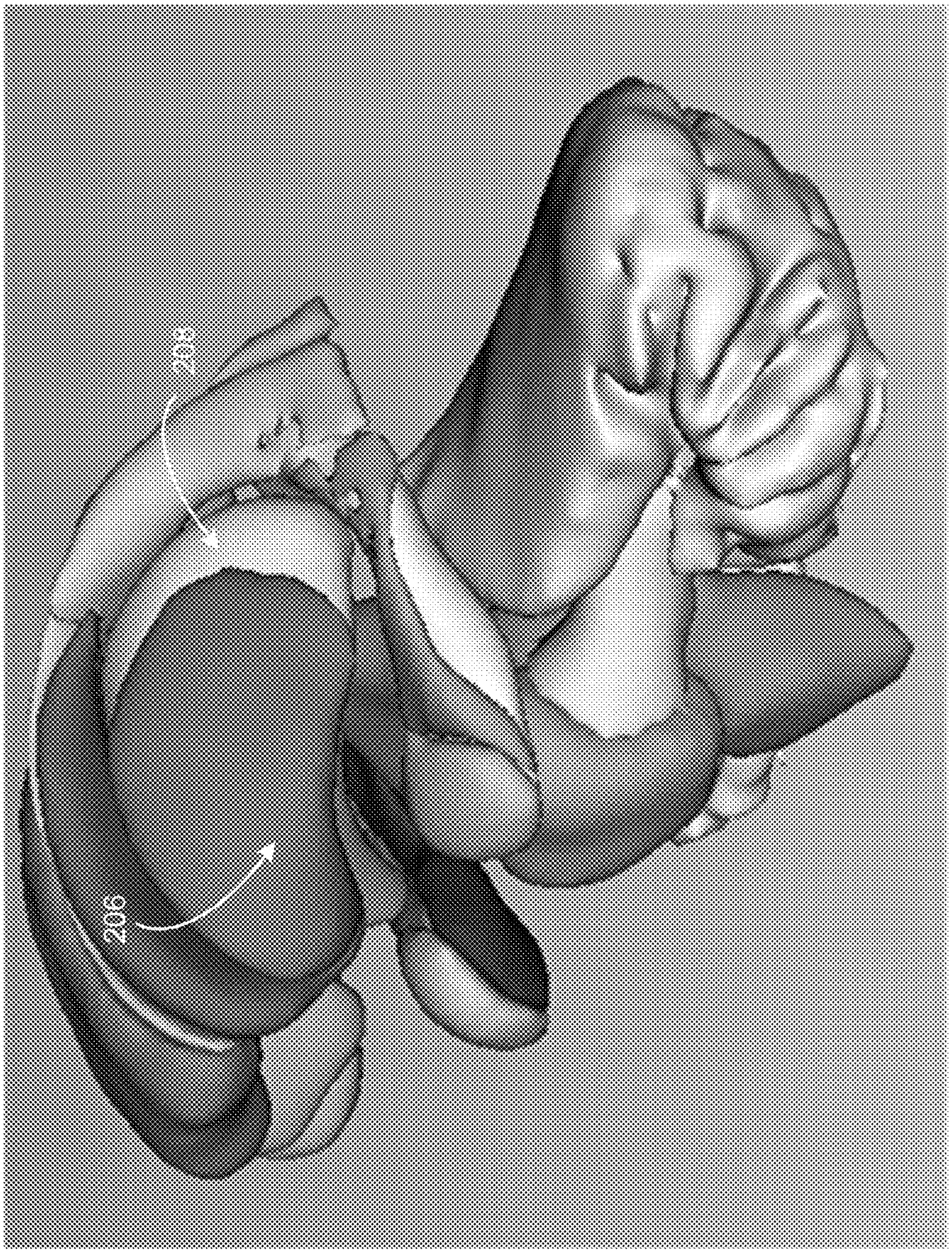
FIG. 2 depicts an example patient-specific brain representation including 3D segments representing sub-cortical brain structures, in accordance with various examples of the presently disclosed technology.

FIG. 2 depicts patient-specific brain representation 100 including 3D segments representing sub-cortical structures of the patient's brain (e.g., patient-specific sub-cortical brain structure representations 206 and 208), in accordance with various examples of the presently disclosed technology.

As alluded to above, patient-specific 3D sub-cortical brain structure representations (e.g., patient-specific 3D sub-cortical brain structure representations 206 and 208) may be 3D segments of patient-specific brain representation 100. Each patient-specific 3D sub-cortical brain structure representation may represent a sub-cortical brain structure of the patient. These sub-cortical brain structures may be located within the cortical hemispheres of the patient. Accordingly, the patient-specific 3D sub-cortical brain structure representations representing these sub-cortical brain structures may be located within patient-specific 3D brain structure representations 102 and 104.

As alluded to above, a first sub-cortical brain structure of a patient (e.g., the sub-cortical brain structure representing by patient-specific 3D sub-cortical brain structure representation 206) may be targeted for surgical intervention. Accordingly, a prospective surgical trajectory may comprise a linear (or approximately linear) path from an entry point for initially entering a patient's brain cortex to a target point located within the first sub-cortical brain structure. As described above, examples can determine a level of safety for the prospective surgical trajectory based on a number of times a prospective surgical trajectory representation (representing the prospective surgical trajectory) intersects a patient-specific 3D cortical surface representation (e.g., 3D cortical surface representation 104*a*) before reaching a representational target point located within a patient-specific 3D sub-cortical brain structure representation representing the first sub-cortical brain structure (e.g., patient-specific 3D sub-cortical brain structure representation 206).

As alluded to above, examples can also determine a level of safety for the prospective surgical trajectory by determining a number of times that the prospective surgical trajectory representation intersects one or more patient-specific 3D hazard brain region representations. Here, a patient-specific 3D hazard brain region representation may represent a hazard brain region to be avoided during surgery (examples of hazard brain regions may including various regions/structures of the patient's brain including blood vessels, sub-cortical brain structures not targeted for surgery, other regions of the brain, etc.). For example, a first sub-cortical brain structure represented by patient-specific sub-cortical brain structure representation 206 may be targeted for surgery. However, a second sub-cortical brain structure represented by patient-specific 3D sub-cortical brain structure representation 208 may be a hazard brain region to be avoided because piercing the second sub-cortical brain structure would cause unnecessary patient trauma or surgical complications. Accordingly, examples can determine a level of safety for the prospective surgical trajectory (to the target point within the first sub-cortical structure) by determining a number of times that the prospective surgical trajectory representation intersects patient-specific 3D sub-cortical brain structure representation 208 (i.e., the 3D hazard brain region representation).

Figure 3:
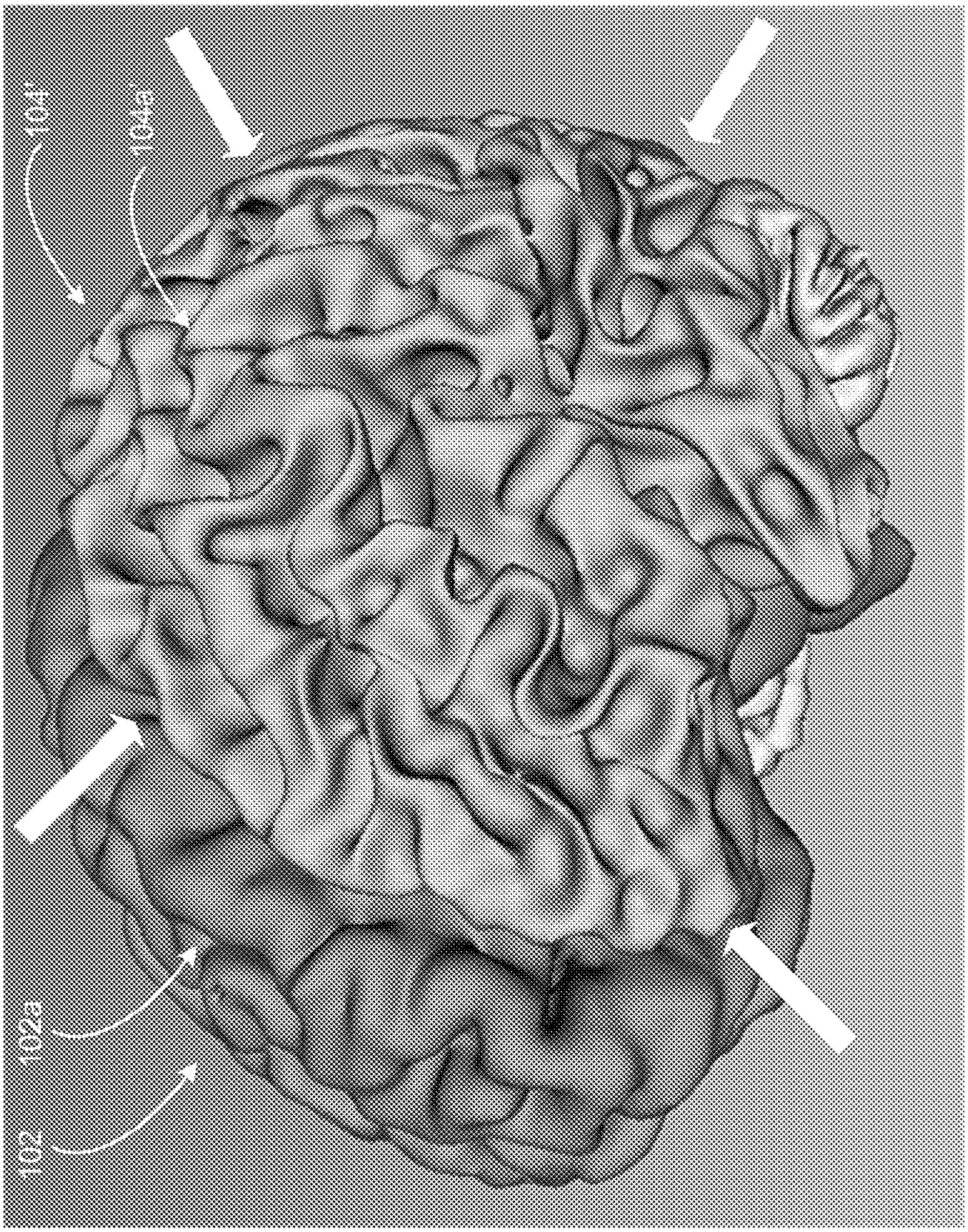
FIG. 3 depicts an example patient-specific brain representation including a safety margin-modified 3D segment representing a cortical hemisphere, in accordance with various examples of the presently disclosed technology.

FIG. 3 depicts example patient-specific brain representation 100 including a safety margin-modified 3D segment representing the left cortical hemisphere (i.e., safety-margin modified 3D patient-specific brain structure representation 104'), in accordance with various examples of the presently disclosed technology.

As described above, examples can leverage computer graphic techniques to incorporate safety margins into pre-advancement trajectory safety evaluations. Examples can utilize these surgical safety margins to determine whether prospective surgical trajectories pass within a minimum acceptable distance to a hazard (e.g., the surface of the brain cortex or other hazard brain regions). For instance, examples can modify the size of the patient-specific 3D cortical surface representation (or in some cases, a patient-specific 3D brain structure representation of which the patient-specific 3D cortical surface representation is a 3D boundary surface) and the patient-specific 3D hazard brain region representations in accordance with a desired safety margin (e.g., the patient-specific 3D cortical surface representation can be reduced in size by an amount corresponding to the desired safety margin and the patient-specific 3D hazard brain region representations can be increased in size by an amount corresponding to the desired safety margin). Examples can then determine whether a prospective surgical trajectory passes within a minimum acceptable distance (as defined by the desired safety margin) to a hazard by determining if (and if so, how many times) a prospective surgical trajectory representation (representing the prospective surgical trajectory) intersects the safety margin-modified patient-specific 3D cortical surface representation and the safety margin-modified patient-specific 3D hazard brain region representations.

Referring again to FIG. 3, safety-margin modified patient-specific 3D brain structure representation 104' is a version of patient-specific 3D brain structure representation 104 (described in conjunction with FIG. 1) modified in accordance with a desired safety margin. In particular, safety-margin modified patient-specific 3D brain structure representation 104' is a version of patient-specific 3D brain structure representation 104 that has reduced in size by an amount corresponding to the desired safety margin. Here, examples may modify patient-specific 3D brain structure representation 104 (as opposed to patient-specific brain structure representation 102—which is not modified in the example of FIG. 3) because a prospective surgical trajectory may require piercing the left cortical hemisphere of the patient (which patient-specific 3D brain structure representation 104 represents). This may be the case because a surgical target point is located within the left cortical hemisphere of the patient.

Here it may be noted that safety-margin modified patient-specific 3D brain structure representation 104' includes a safety margin-modified patient specific 3D cortical surface representation 104*a*'. As described above, examples can determine/estimate a number of times that a prospective surgical trajectory will pass within a minimum acceptable distance (as defined by the desired safety margin) to the cortical surface of the left cortical hemisphere by determining a number of times a prospective surgical trajectory representation (representing the prospective surgical trajectory) intersects safety margin-modified patient specific 3D cortical surface representation 104*a*'. In other words, each time the prospective surgical trajectory representation intersects safety margin-modified patient specific 3D cortical surface representation 104*a*' may represent an instance where the prospective surgical trajectory passes within the minimum acceptable distance (as defined by the desired safety margin) to the cortical surface of the left cortical hemisphere.

As described, examples can utilize various computer graphics-related techniques to reduce patient-specific 3D brain structure representation 104 in size to form safety-margin modified patient-specific 3D brain structure representation 104'. For instance, examples can apply an erosion filter to remove voxels of patient-specific 3D brain structure representation 104 lying in proximity to 3D cortical surface representation 104*a*. In this way, examples can effectively remove/shave-off the outer-most volume of patient-specific 3D brain structure representation 104 in order to form (size-reduced) safety-margin modified patient-specific brain structure representation 104'. In other instances, examples can inwardly displace individual voxels of 3D cortical surface representation 104*a* by a set amount along downwards projections from the individual voxels' surface normals. In this way, examples can inwardly contract patient-specific 3D brain structure representation 104 in order to form (size-reduced) safety-margin modified patient-specific 3D brain structure representation 104'.

While not depicted, examples can increase patient-specific 3D hazard brain region representation in size by an amount corresponding to the desired safety margin using similar techniques. For instance, examples can apply a dilation filter to a given patient-specific 3D hazard brain region representation to outwardly expand the given patient-specific 3D hazard brain region representation voxel-wise. In other instances, examples can displace individual voxels of a 3D boundary surface of the given patient-specific 3D hazard region representation by a set amount along the individual voxels' surface normals (here the 3D boundary surface of the given patient-specific 3D hazard region representation may represent the exterior boundary surface of a given hazard brain region represented by the given patient-specific 3D hazard region representation). As described above, examples can determine/estimate a number of times that a prospective surgical trajectory will pass within a minimum acceptable distance (as defined by the desired safety margin) to the given hazard brain region by determining a number of times a prospective surgical trajectory representation (representing the prospective surgical trajectory) intersects a safety margin-modified (i.e., size-increased) version of the given patient-specific 3D hazard brain region representation. In other words, each time the prospective surgical trajectory representation intersects the safety margin-modified (i.e., size-increased) version of the given patient-specific 3D hazard brain region representation may represent an instance where the prospective surgical trajectory passes within the minimum acceptable distance (as defined by the desired safety margin) to the given hazard brain region.

Figure 4:
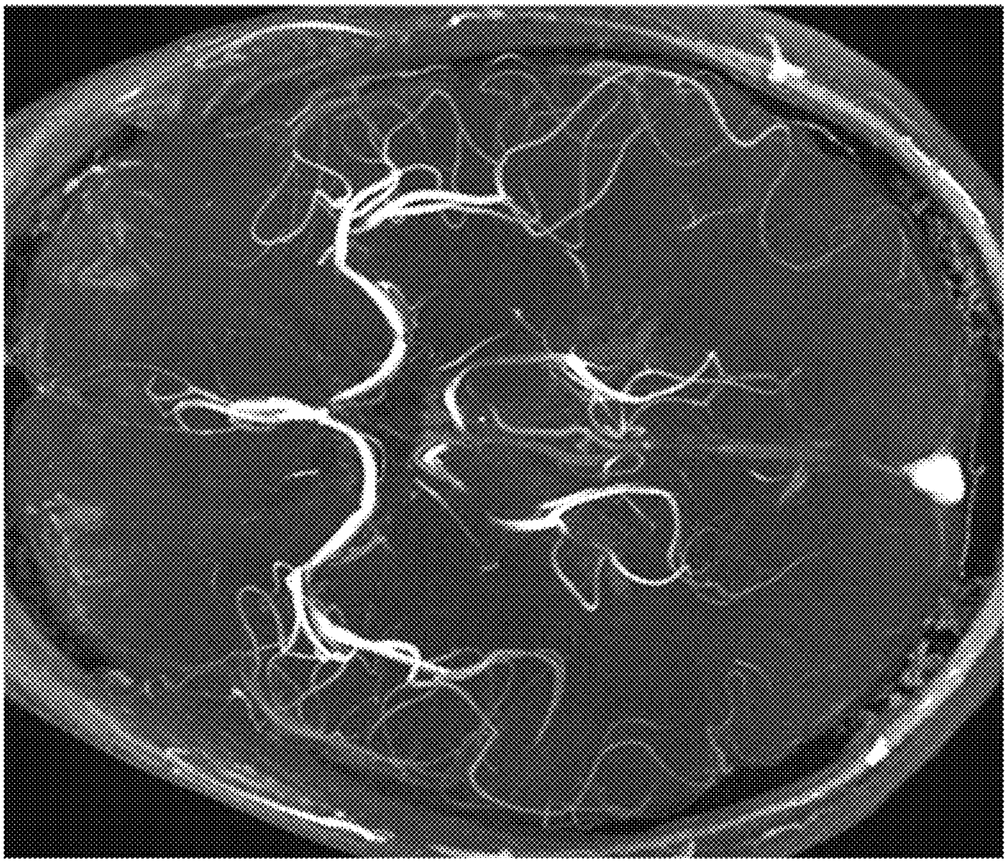
FIG. 4 depicts an example magnetic resonance angiography (MRA) image showing blood vessel contrast, in accordance with various examples of the presently disclosed technology.

FIG. 4 depicts an example magnetic resonance angiography (MRA) image showing blood vessel contrast, in accordance with various examples of the presently disclosed technology.

As alluded to above, individual blood vessels can be hazard brain regions to be avoided during surgery. Accordingly, in various examples technologies such as MRA can be used to identify blood vessels. With the blood vessels identified, examples can generate patient-specific 3D hazard brain region representations that represent the identified blood vessels.

Figure 5:
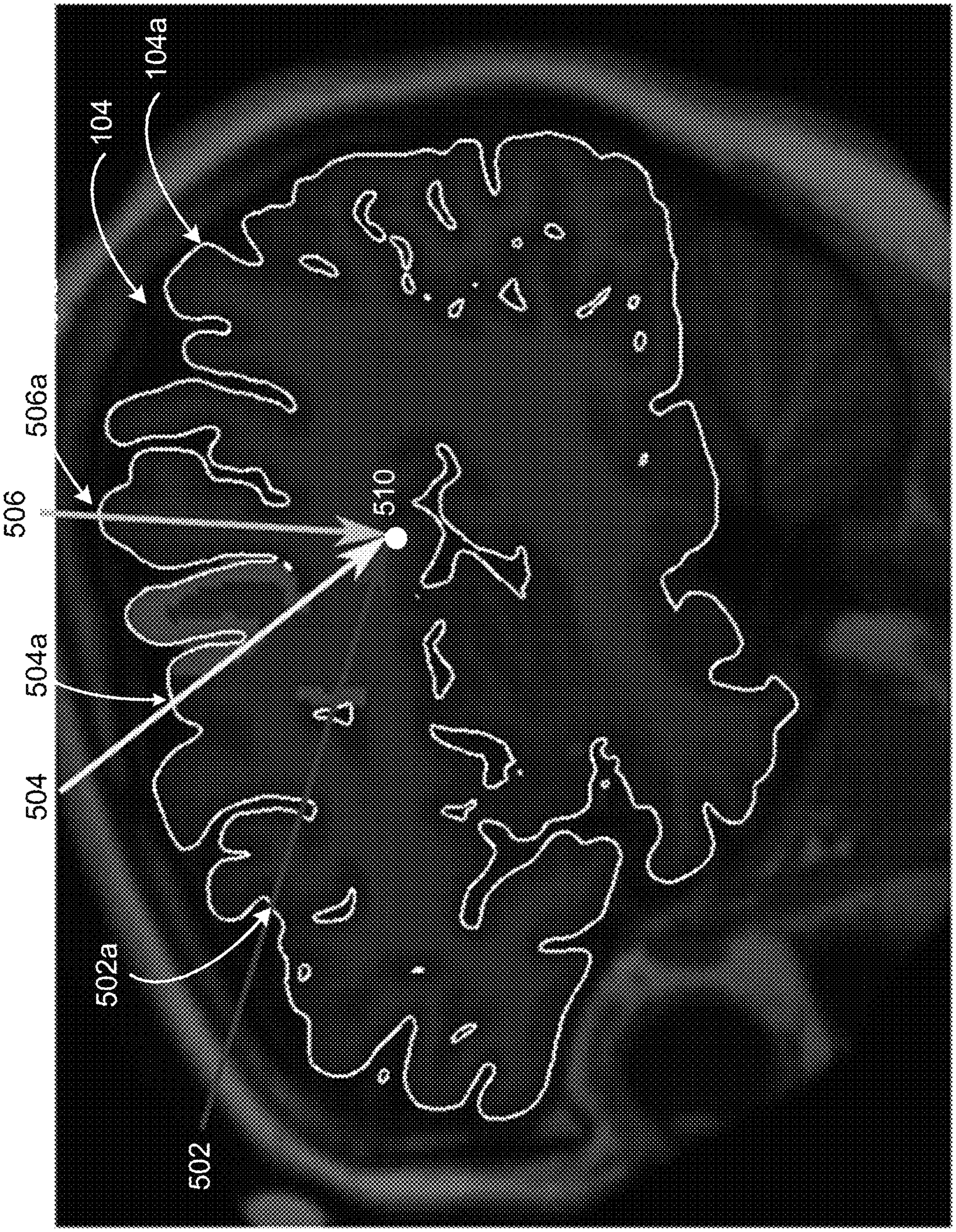
FIG. 5 depicts example prospective surgical trajectory representations, in accordance with various examples of the presently disclosed technology.

FIG. 5 depicts examples prospective surgical trajectory representations, in accordance with various examples of the presently disclosed technology.

As depicted, FIG. 5 depicts three prospective surgical trajectory representations: prospective surgical trajectory representations 502, 504, and 506.

FIG. 5 also depicts patient-specific 3D brain structure representation 104 and patient-specific 3D cortical surface representation **104*a* described in conjunction with FIG. 1. As depicted, a target point 510 may be located within the patient's left cortical hemisphere represented by patient-specific 3D brain structure representation 104**.

As described above, a prospective surgical trajectory may comprise a linear (or approximately linear) path that connects a prospective entry point for initially entering a patient's brain structure (e.g., the patient's left cortical hemisphere) and a target point located within the brain structure (e.g., a target point in a sub-cortical brain structure located within the patient's left cortical hemisphere). Accordingly, a prospective surgical trajectory representation (representing the prospective surgical trajectory) may comprise a 1D line that represents the prospective surgical trajectory. As depicted in FIG. 5, prospective surgical trajectory representation 502 may be a 1D line that represents a prospective surgical trajectory that connects a prospective entry point **502*a* (for initially entering the patient's left cortical hemisphere) and target point 510. Likewise, prospective surgical trajectory representation 504 may be a 1D line that represents a prospective surgical trajectory that connects a prospective entry point 504*a* (for initially entering the patient's left cortical hemisphere) and target point 510. Similarly, prospective surgical trajectory representation 506 may be a 1D line that represents a prospective surgical trajectory that connects a prospective entry point 506*a* (for initially entering the patient's left cortical hemisphere) and target point 510**.

As described above, examples can determine a level of safety for a prospective surgical trajectory by determining/estimating a number of times a surgical instrument advanced along the prospective surgical trajectory would pierce the cortical surface (here, prospective surgical trajectories that would cause a surgical instrument to pierce the cortical surface multiple times may be less safe as the likelihood of piercing a blood vessel located on the cortical surface is increased). Examples can make this determination/estimation by determining a number of times a prospective surgical trajectory representation (representing the prospective surgical trajectory) intersects a patient-specific 3D cortical surface representation (e.g., 3D cortical surface representation **104*a***).

Relatedly, examples can also determine a level of safety for a prospective surgical trajectory by determining/estimating a number of times (and/or the extent to which) a surgical instrument advanced along the prospective surgical trajectory would pass within a minimum acceptable distance (as defined by a desired safety margin) to the cortical surface. Examples can make this determination/estimation by determining a number of times (and/or the extent to which) the prospective surgical trajectory representation (representing the prospective surgical trajectory) passes within a minimum acceptable distance to the patient-specific 3D cortical surface representation (e.g., 3D cortical surface representation **104*a***).

As depicted, prospective surgical trajectory representation 506 intersects patient-specific 3D cortical surface representation **104*a* only once. Relatedly, prospective surgical trajectory representation 506 does not generally pass very closely to patient-specific 3D cortical surface representation 104*a* after the initial intersection. Accordingly, prospective surgical trajectory representation 502 may maintain a minimum acceptable distance (as defined by a desired safety margin) from patient-specific 3D cortical surface representation 104*a*. Accordingly, examples may determine that the prospective surgical trajectory represented by prospective surgical trajectory representation 502 is a "safe" surgical trajectory due to a reduced likelihood that a surgical instrument advanced along the prospective surgical trajectory would pierce the cortical surface multiple times. Using the "traffic light" type notification alluded to above, examples may provide a green light notification for the prospective surgical trajectory represented by prospective surgical trajectory representation 506**.

As depicted, prospective surgical trajectory representation 504 intersects patient-specific 3D cortical surface representation **104*a* only once as well. However, prospective surgical trajectory representation 504 passes very closely to patient-specific 3D cortical surface representation 104*a* after the initial intersection. Accordingly, multiple points along prospective surgical trajectory representation 504 may pass within a minimum acceptable distance (as defined by a desired safety margin) to patient-specific 3D cortical surface representation 104***a*. Accordingly, examples may determine that the prospective surgical trajectory represented by prospective surgical trajectory representation 504 is a "less safe" surgical trajectory (as compared to the prospective surgical trajectory represented by prospective surgical trajectory representation 506) due to a heightened likelihood that a surgical instrument advanced along the prospective surgical trajectory would pierce the cortical surface multiple times. Using the "traffic light" type notification alluded to above, examples may provide a yellow light notification for the prospective surgical trajectory represented by prospective surgical trajectory representation 504.

As depicted, prospective surgical trajectory representation 502 intersects patient-specific 3D cortical surface representation 104*a* five times. Based on this high number of intersections, examples may determine that the prospective surgical trajectory represented by prospective surgical trajectory representation 502 is a "hazardous" surgical trajectory. Using the "traffic light" type notification alluded to above, examples may provide a red light notification for the prospective surgical trajectory represented by prospective surgical trajectory representation 502.

Figure 6:
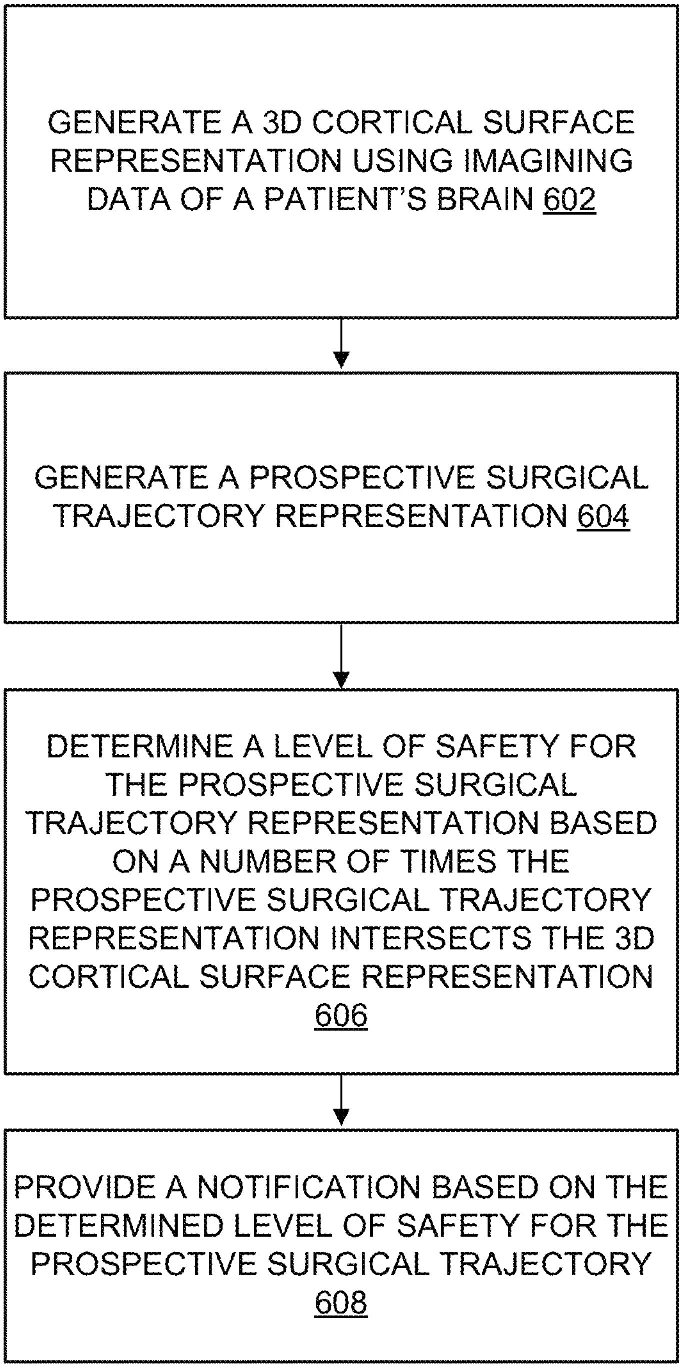
FIG. 6 depicts an example flow diagram that may be used to determine a level of safety for a prospective surgical trajectory, in accordance with various examples of the presently disclosed technology.

FIG. 6 depicts an example flow diagram that may be used to determine a level of safety for a prospective surgical trajectory, in accordance with various examples of the presently disclosed technology.

At operation 602, examples generate a 3D cortical surface representation using imaging data of a patient's brain. The 3D cortical surface representation may represent a cortical surface of a brain structure of the patient. In certain instances, the brain structure of the patient may be a cortical hemisphere of the patient (e.g., the left or right cortical hemisphere of the patient).

Examples can generate the 3D cortical surface representation from imaging data of the patient's brain using any of the techniques described in conjunction with FIG. 1. For instance, examples can first generate a patient-specific brain representation (i.e., a computerized 3D representation of the patient's brain comprised of individual 3D segments representing various structures of the patient's brain) by adapting a generalized brain representation (i.e., a non-patient-specific representation of the human brain) to the imaging data of the patient's brain (e.g., MR or CT scans of the patient's brain obtained before or during a surgical intervention).

Here, the generated patient-specific brain representation may include a segment/3D (volumetric) representation for the brain structure of the patient. The 3D cortical surface representation may be a 3D boundary surface of the 3D representation for the brain structure. In certain cases, examples can generate the 3D cortical surface representation by applying a marching cubes algorithm to the 3D representation for the brain structure.

As described in conjunction with FIG. 1, in certain cases the 3D representation for the brain structure may comprise a 3D mesh representation and the 3D cortical surface representation may comprise a 3D mesh boundary surface. These 3D meshes may preserve point-based correspondences between mesh vertices of the generalized brain representation and mesh vertices of the patient-specific 3D meshes. These point-based correspondences can be used to identify the various brain structures of the patient.

At operation 604, examples generate a prospective surgical trajectory representation that represents a prospective surgical trajectory.

In certain cases, examples may generate the prospective surgical trajectory in response to user input that identifies a target point within the brain structure and a prospective entry point for entering the brain structure. Accordingly, the prospective surgical trajectory may be a 1D line that intersects the target point and the prospective entry point.

At operation 606, examples determine a level of safety for the prospective surgical trajectory based on a number of times the prospective surgical trajectory representation intersects the 3D cortical surface representation.

As described above, examples can determine a level of safety for a prospective surgical trajectory by determining/estimating a number of times a surgical instrument advanced along the prospective surgical trajectory would pierce the cortical surface (here, prospective surgical trajectories that would cause a surgical instrument to pierce the cortical surface multiple times may be less safe as the likelihood of piercing a blood vessel located on the cortical surface is increased). Examples can make this determination/estimation by determining a number of times the prospective surgical trajectory representation (representing the prospective surgical trajectory) intersects the 3D cortical surface representation (representing the cortical surface of the patient).

At operation 608, examples can provide a notification (to e.g., a neurosurgeon, administering clinician, etc.) based on the determined level of safety for the prospective surgical trajectory. Based on this notification, a neurosurgeon can apply their clinical judgment/expertise as a final level of review prior to advancing a surgical instrument along the prospective surgical trajectory (if the prospective surgical trajectory is determined to be safe) or selecting a new/safer prospective surgical trajectory. By allowing a neurosurgeon to focus their efforts/expertise on final analysis of an automated safety evaluation, examples can significantly reduce intervention times, improve patient safety, and increase access to certain brain surgeries.

As described above, in various cases the provided notification may comprise a "traffic light" type notification. For example, a green light may indicate a "safe" surgical trajectory that pierces the cortical surface just a single time while avoiding hazard brain regions (and in some cases, not passing within a minimum acceptable distance to hazard brain regions). A yellow light may indicate a "less safe" surgical trajectory that e.g., passes closely to hazard brain regions and/or pierces the surface of the cortical surface multiple times. A red light may indicate a "hazardous" surgical trajectory that e.g., pierces one or more hazard brain regions and/or pierces the cortical surface multiple times. As described above, these notifications can be provided to a neurosurgeon in real-time (or approximately real-time) thereby reducing surgical intervention/planning times and improving patient safety.

Figure 7:
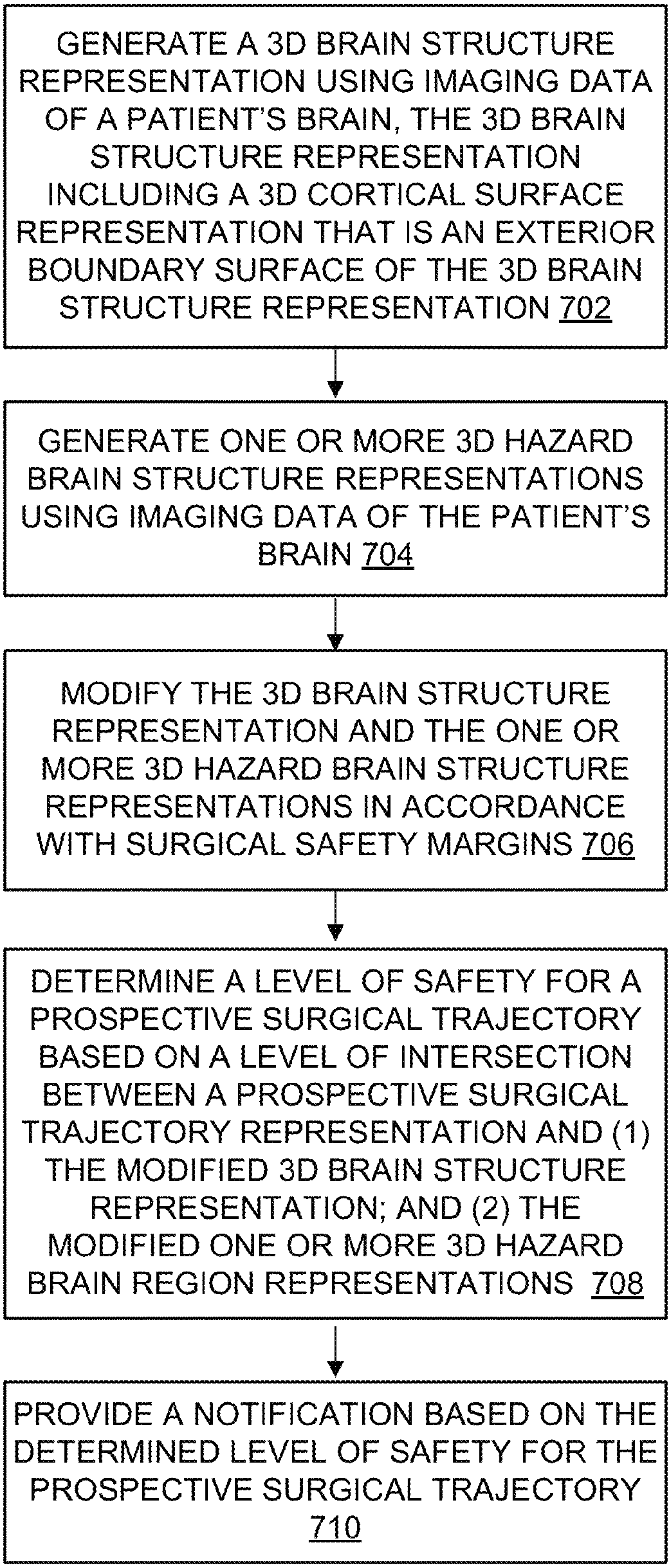
FIG. 7 depicts another example flow diagram that may be used to determine a level of safety for a prospective surgical trajectory, in accordance with various examples of the presently disclosed technology.

FIG. 7 depicts another example flow diagram that may be used to determine a level of safety for a prospective surgical trajectory, in accordance with various examples of the presently disclosed technology.

At operation 702, examples generate a 3D brain structure representation using imaging data of a patient's brain—the 3D brain structure representation including a 3D cortical surface representation that is an exterior boundary surface of the 3D brain structure representation. Here the 3D brain structure representation may represent a brain structure of the patient, and the 3D cortical surface representation may represent the cortical surface of the brain structure.

Examples may generate the 3D brain structure representation and the 3D cortical surface representation using the same/similar techniques as described in the preceding figures.

At operation 704, examples generate one or more 3D hazard brain region representations using imaging data of the patient's brain. Examples can generate these 3D hazard brain regions using any of the techniques described in conjunction with the preceding figures.

As described above (and as will be described below in conjunction with operation 708), examples can determine a level of safety for a prospective surgical trajectory by determining a number of times that a prospective surgical trajectory representation (representing the prospective surgical trajectory) intersects the one or more 3D hazard brain region representations. Here, a given 3D hazard brain region representation may represent a hazard brain region of the patient to be avoided during surgery (examples of hazard brain regions may including various regions/structures of the patient's brain including blood vessels, sub-cortical structures not targeted for surgery, other regions of the brain, etc.). For example, a first sub-cortical structure within the brain structure may be targeted for surgery (here a prospective surgical trajectory may connect a target point within the first sub-cortical structure, and an initial entry point for entering the patient's brain structure). However, a second sub-cortical structure located proximate to the first sub-cortical structure may be a hazard brain region to be avoided because piercing the second sub-cortical structure would cause unnecessary patient trauma or surgical complications. Accordingly, examples can determine a level of safety for a prospective surgical trajectory (to the target point within the first sub-cortical structure) by determining a number of times that a prospective surgical trajectory representation (representing the prospective surgical trajectory) intersects a 3D representation of the second sub-cortical structure (i.e., a 3D hazard brain region representation). As alluded to above, the number of times the prospective surgical trajectory representation intersects the 3D representation of the second sub-cortical structure can serve as an estimate/proxy for a number of times a surgical instrument advanced along the prospective surgical trajectory would pierce the second sub-cortical structure (i.e. the hazard brain region of the patient).

At operation 706, examples modify the 3D brain structure representation and the one or more 3D hazard brain region representations in accordance with surgical safety margins.

As described above, examples can utilize surgical safety margins to determine an extent to which prospective surgical trajectories pass within a minimum acceptable distance to a hazard (e.g., the cortical surface or other hazard brain regions). Examples can leverage various computer graphic techniques to incorporate these safety margins into prospective trajectory safety evaluations.

For example, and as described in conjunction with operation 706, examples can modify the 3D brain structure representation and the one or more 3D hazard brain region representations in accordance with the surgical safety margins. In certain cases, this may involve (1) reducing the 3D brain structure representation (and/or the 3D cortical surface representation) in size in accordance with the surgical safety margins; and (2) increasing the 3D hazard brain region representations in size in accordance with the surgical safety margins. Examples can then determine an extent to which a prospective surgical trajectory passes within a minimum acceptable distance (as defined by the desired safety margin) to a hazard by determining a level of intersection between a prospective surgical trajectory representation representing the prospective surgical trajectory and: (1) the safety margin-modified (i.e., size-reduced) 3D brain structure representation; and (2) the safety margin-modified (i.e. size-increased) 3D hazard brain region representations. Here "a level of intersection" may be a numerical value measuring a level of intersection such as a number of intersections between the prospective surgical trajectory representation and safety margin-modified hazard representation, a percentage of the prospective surgical representation that intersects safety margin-modified hazard representations, etc.).

Examples can use various computer graphic techniques to reduce the 3D brain structure representation in size in accordance with the surgical safety margins. For instance, examples can apply an erosion filter to remove voxels of the 3D brain structure representation lying in proximity to the outer boundary of the 3D brain structure representation. In this way, examples can effectively remove/shave-off the outer-most volume of the 3D brain structure representation in order to form a (size-reduced) safety-margin modified 3D brain structure representation. In other instances, examples can inwardly displace individual voxels of the 3D cortical surface representation by a set amount along downwards projections from the individual voxels' surface normals. In this way, examples can inwardly contract the 3D brain structure representation in order to form the (size-reduced) safety-margin modified 3D brain structure representation.

Examples can increase the one or more 3D hazard brain region representations in size using similar techniques. For instance, examples can apply a dilation filter to a given 3D hazard brain region representation to outwardly expand the given 3D hazard brain region representation voxel-wise. In other instances, examples can displace individual voxels of a 3D boundary surface of the given 3D hazard region representation by a set amount along the individual voxels' surface normals (here the 3D boundary surface of the given 3D hazard region representation may represent the exterior boundary surface of a given hazard brain region represented by the given 3D hazard region representation). As described above, examples can determine/estimate an extent to which a prospective surgical trajectory will pass within a minimum acceptable distance (as defined by the surgical safety margins) to the given hazard brain region by determining a level of intersection between a prospective surgical trajectory representation (representing the prospective surgical trajectory) and a (size-increased) safety margin-modified version of the given 3D hazard brain region representation. For example, individual point of the prospective surgical trajectory representation that intersects the (size-increased) safety margin-modified version of the given 3D hazard brain region representation may represent a point of the prospective surgical trajectory that passes within the minimum acceptable distance (as defined by the surgical safety margin) to the given hazard brain region (here instances where the prospective surgical trajectory actually intersects/pierces a hazard may be considered instances which the prospective surgical trajectory passes within the minimum acceptable distance to the hazard).

As alluded to above, at operation 710, examples determine a level of safety for a prospective surgical trajectory based on a level of intersection between a prospective surgical trajectory representation representing the prospective surgical trajectory and: (1) the (safety margin) modified 3D brain structure representation; and (2) the (safety margin) modified one or more 3D hazard brain region representations.

As alluded to above, the level of intersection between the prospective surgical trajectory representation and the modified 3D brain structure representation can be an estimate of an extent to which a surgical instrument advanced along the prospective surgical trajectory (represented by prospective surgical trajectory representation) would pass within a minimum acceptable distance to the cortical surface. Similarly, the level of intersection between the prospective surgical trajectory representation and the modified one or more 3D hazard brain region representations can be an estimate of an extent to which a surgical instrument advanced along the prospective surgical trajectory (represented by prospective surgical trajectory representation) would pass within a minimum acceptable distance to the one or more hazard brain regions. In general, safer prospective surgical trajectories will pass within the minimum acceptable distance to these hazards to the least extent as possible.

At operation 710, examples provide a notification based on the determined level of safety for the prospective surgical trajectory. This operation may be performed in the same/similar manner as described in conjunction with FIG. 6.

Figure 8:
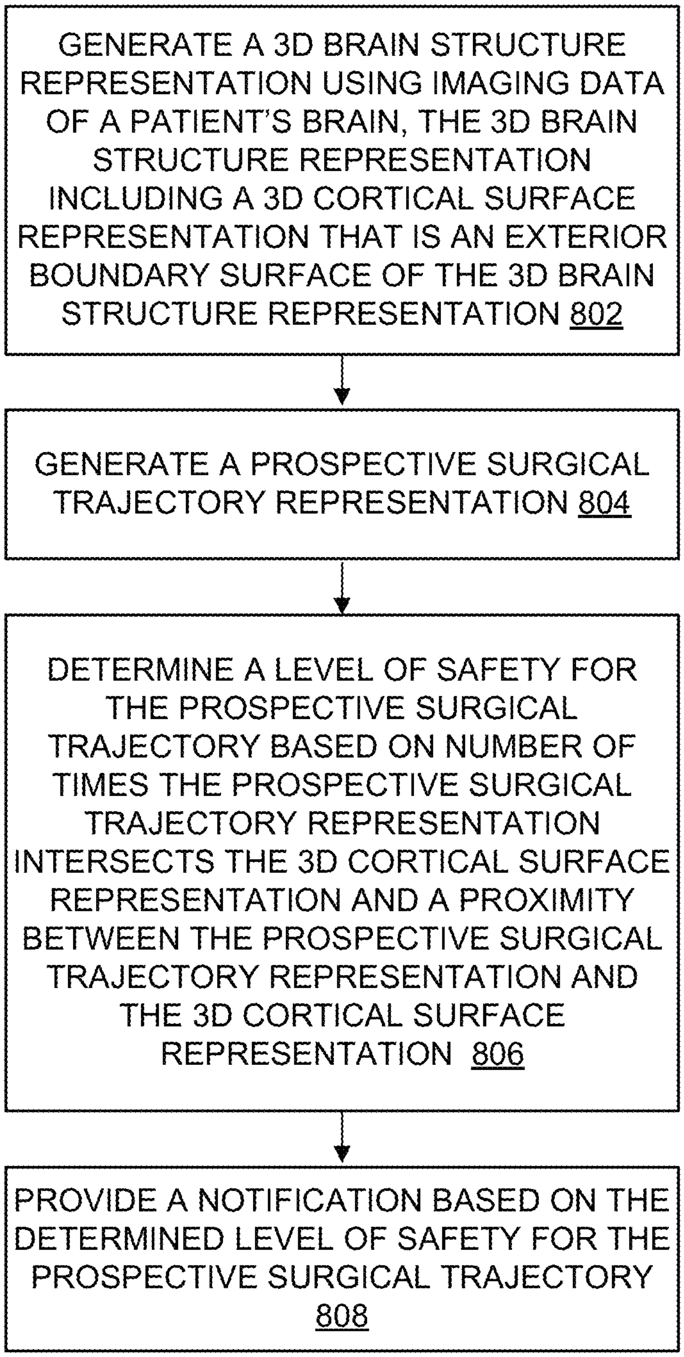
FIG. 8 depicts another example flow diagram that may be used to determine a level of safety for a prospective surgical trajectory, in accordance with various examples of the presently disclosed technology.

FIG. 8 depicts another example flow diagram that may be used to determine a level of safety for a prospective surgical trajectory, in accordance with various examples of the presently disclosed technology.

At operation 802, examples generate a 3D brain structure representation using imaging data of a patient's brain—the 3D brain structure representation including a 3D cortical surface representation that is an exterior boundary surface of the 3D brain structure representation. Here the 3D brain structure representation may represent a brain structure of the patient, and the 3D cortical surface representation may represent the cortical surface of the brain structure.

Examples may generate the 3D brain structure representation and 3D cortical surface representation using the same/similar techniques as described in the preceding figures.

At operation 804, in response to user input that identifies a target point within the brain structure and a prospective entry point for initially entering the brain structure, examples generate a prospective surgical trajectory representation, the prospective surgical trajectory representation representing a prospective surgical trajectory that connects the prospective entry point and the target point. Here the prospective surgical trajectory may be a 1D line that intersects the target point and the prospective entry point.

At operation 806, examples determining a level of safety for the prospective surgical trajectory based on a number of times the prospective surgical trajectory representation intersects the 3D cortical surface representation and a proximity between the prospective surgical trajectory representation and the 3D cortical surface representation. In certain instances, this may comprise (1) computing point-to-surface distances between the prospective surgical trajectory representation and the 3D cortical surface representation; and (2) comparing the computed distances to threshold safety margin distances—to estimate whether (and/or to what extent) the prospective surgical trajectory passes closer than a minimum acceptable distance to the cortical surface of the patient's brain structure.

In certain cases the prospective surgical trajectory representation may comprise a 1D line. In these cases, threshold safety margin distances may be based in part on diameter of a surgical tool to be inserted into the brain structure along the prospective surgical trajectory.

In certain cases, examples may also generate one or more 3D hazard brain region representations using imaging data of the patient's brain, a given 3D hazard brain region representation representing a given hazard brain region to be avoided during surgery. Accordingly, in these cases operation 806 may comprise further comprise determining the level of safety for the prospective surgical trajectory based on a number of times the prospective surgical trajectory representation intersects the one or more 3D hazard brain region representations and a proximity of the prospective surgical trajectory representation to the one or more 3D hazard brain region representations. In certain cases, this determination may comprise determining an extent to which the prospective surgical trajectory representation passes within a threshold distance to the one or more 3D hazard brain region representations. Here, determining the extent to which the prospective surgical trajectory representation passes within a threshold distance to the one or more 3D hazard brain region representations may comprise: (1) computing, for each individual point of the prospective surgical trajectory representation, distance to 3D boundary surfaces of the one or more 3D hazard brain region representations, a given 3D boundary surface of a given 3D hazard brain region representation representing an exterior boundary surface for a given hazard brain region represented by the given 3D hazard brain region representation; and (2) determining a number of computed distances that are less than the threshold distance.

At operation 808, examples provide a notification based on the determined level of safety for the prospective surgical trajectory. This operation may be performed in the same/similar manner as described in conjunction with FIG. 6.

Figure 9:
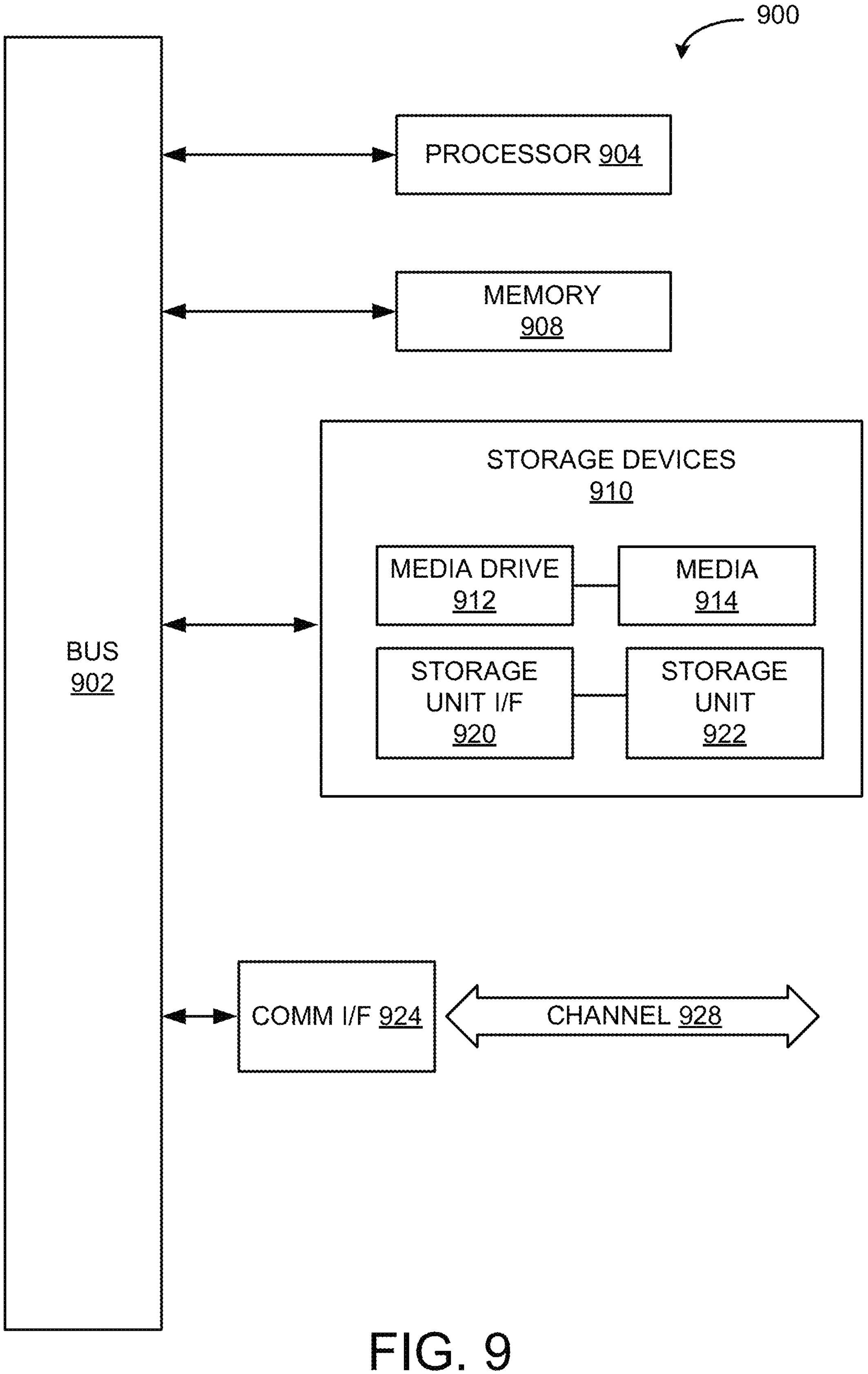
FIG. 9 is an example computing component that may be used to implement various features of examples described in the present disclosure.

As used herein, the terms circuit and component might describe a given unit of functionality that can be performed in accordance with one or more examples of the present application. As used herein, a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component. Various components described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and permutations. Although various features or functional elements may be individually described or claimed as separate components, it should be understood that these features/functionality can be shared among one or more common software and hardware elements. Such a description shall not require or imply that separate hardware or software components are used to implement such features or functionality.

Where components are implemented in whole or in part using software, these software elements can be implemented to operate with a computing or processing component capable of carrying out the functionality described with respect thereto. One such example computing component is shown in FIG. 9. Various examples are described in terms of this example-computing component 910. After reading this description, it will become apparent to a person skilled in the relevant art how to implement the application using other computing components or architectures.

Referring now to FIG. 9, computing component 910 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 910 might also represent computing capabilities embedded within or otherwise available to a given device. For example, a computing component might be found in other electronic devices such as, for example, portable computing devices, and other electronic devices that might include some form of processing capability.

Computing component 910 might include, for example, one or more processors, controllers, control components, or other processing devices. Processor 914 might be implemented using a general-purpose or special-purpose processing engine such as, for example, a microprocessor, controller, or other control logic. Processor 914 may be connected to a bus 912. However, any communication medium can be used to facilitate interaction with other components of computing component 910 or to communicate externally.

Computing component 910 might also include one or more memory components, simply referred to herein as main memory 918. For example, random access memory (RAM) or other dynamic memory, might be used for storing information and instructions to be executed by processor 914. Main memory 918 might also be used for storing temporary variables or other intermediate information during execution of instructions to be executed by processor 914. Computing component 910 might likewise include a read only memory ("ROM") or other static storage device coupled to bus 912 for storing static information and instructions for processor 914.

The computing component 910 might also include one or more various forms of information storage mechanism 191, which might include, for example, a media drive 192 and a storage unit interface 920. The media drive 192 might include a drive or other mechanism to support fixed or removable storage media 914. For example, a hard disk drive, a solid-state drive, a magnetic tape drive, an optical drive, a compact disc (CD) or digital video disc (DVD) drive (R or RW), or other removable or fixed media drive might be provided. Storage media 914 might include, for example, a hard disk, an integrated circuit assembly, magnetic tape, cartridge, optical disk, a CD or DVD. Storage media 914 may be any other fixed or removable medium that is read by, written to or accessed by media drive 192. As these examples illustrate, the storage media 914 can include a computer usable storage medium having stored therein computer software or data.

In alternative examples, information storage mechanism 191 might include other similar instrumentalities for allowing computer programs or other instructions or data to be loaded into computing component 910. Such instrumentalities might include, for example, a fixed or removable storage unit 922 and an interface 920. Examples of such storage units 922 and interfaces 920 can include a program cartridge and cartridge interface, a removable memory (for example, a flash memory or other removable memory component) and memory slot. Other examples may include a PCMCIA slot and card, and other fixed or removable storage units 922 and interfaces 920 that allow software and data to be transferred from storage unit 922 to computing component 910.

Computing component 910 might also include a communications interface 924. Communications interface 924 might be used to allow software and data to be transferred between computing component 910 and external devices. Examples of communications interface 924 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 924 may be carried on signals, which can be electronic, electromagnetic (which includes optical) or other signals capable of being exchanged by a given communications interface 924. These signals might be provided to communications interface 924 via a channel 928. Channel 928 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 918, storage unit 920, media 914, and channel 928. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 910 to perform features or functions of the present application as discussed herein.

It should be understood that the various features, aspects and functionality described in one or more of the individual examples are not limited in their applicability to the particular example with which they are described. Instead, they can be applied, alone or in various combinations, to one or more other examples, whether or not such examples are described and whether or not such features are presented as being a part of a described example. Thus, the breadth and scope of the present application should not be limited by any of the above-described exemplary examples.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various examples set forth herein are described in terms of exemplary block diagrams, flow charts and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

The invention claimed is:

1. A method, comprising:

adapting a generalized three-dimensional (3D) brain representation to imaging data of a patient's brain to generate a patient-specific 3D brain representation representing the patient's brain;

modifying the patient-specific 3D brain representation in accordance with surgical safety margins by at least one of:

applying an erosion filter to remove outermost voxels at an exterior boundary surface of the patient-specific 3D brain representation, or inwardly displacing individual voxels from the exterior boundary surface of the patient-specific 3D brain representation by a set amount along downwards projections from surface normals of the individual voxels, wherein the exterior boundary surface of the patient-specific 3D brain representation represents a cortical surface of the patient's brain and modifying the patient-specific 3D brain representation maintains size of a sub-cortical structure representation of the patient-specific 3D brain representation representing a sub-cortical structure of the patient's brain being targeted for surgery;

generating a bit mask from the modified patient-specific 3D brain representation;

generating a modified patient-specific 3D cortical surface representation representing a safety margin-modified cortical surface of the patient's brain by applying a marching cubes algorithm to the bit mask;

generating a prospective surgical trajectory representation that represents a prospective surgical trajectory;

determining a level of safety for the prospective surgical trajectory based on a number of times the prospective surgical trajectory representation intersects the modified patient-specific 3D cortical surface representation, wherein the determined level of safety increases with a decreasing number of times the prospective surgical trajectory representation intersects the modified patient-specific 3D cortical surface representation; and generating and displaying, on a graphical user interface (GUI), the prospective surgical trajectory representation overlaying a visual representation of the patient's brain with a visual indicator indicating the determined level of safety for the prospective surgical trajectory.

2. The method of claim 1, wherein:

the 3D hazard brain region represents a second sub-cortical structure.

3. The method of claim 1, wherein the visual representation of the patient's brain comprises at least one of:

the patient-specific 3D mesh cortical surface representation; or a scan of the patient's brain, wherein the imagining data comprises the scan.

4. The method of claim 1, wherein the visual indicator comprises color-coding for the prospective surgical trajectory representation that indicates the determined level of safety for the prospective surgical trajectory.

5. The method of claim 4, wherein the visual indicator comprises color-coding comprises traffic light-related notification wherein:

a green version of the prospective surgical trajectory representation indicates a first level of safety;

a yellow version of the prospective surgical trajectory representation indicates a second level of safety lower than the first level of safety; and a red version of the prospective surgical trajectory representation indicates a third level of safety lower than the second level of safety.

6. The method of claim 1, wherein:

the method further comprises generating a 3D hazard brain region representation using imaging data of the patient's brain, the 3D hazard brain region representation representing a hazard brain region of the patient's brain to be avoided during surgery; and determining the level of safety for the prospective surgical trajectory further comprises determining the level of safety for the prospective surgical trajectory based on a number of times the prospective surgical trajectory representation intersects the 3D hazard brain region representation.

7. The method of claim 6, wherein the 3D hazard brain region representation represents one or more blood vessels located on or within the patient's.

8. The method of claim 6, wherein:

the prospective surgical trajectory representation is generated in response to user input that identifies a target point within the sub-cortical structure of the patient's brain and a prospective entry point for initially entering the patient's brain, the prospective surgical trajectory connecting the target point and the prospective entry point.

9. Non-transitory computer-readable storage media comprising instructions that, when executed by at least one processor of a computing system, cause the computing system to perform a method comprising:

adapting a generalized three-dimensional (3D) brain representation to imaging data of a patient's brain to generate a patient-specific 3D brain representation representing the patient's brain;

modifying the patient-specific 3D brain representation in accordance with surgical safety margins by at least one of:

applying an erosion filter to remove outermost voxels at an exterior boundary surface of the patient-specific 3D brain representation, or inwardly displacing individual voxels from the exterior boundary surface of the patient-specific 3D brain representation by a set amount along downwards projections from surface normals of the individual voxels, wherein the exterior boundary surface of the patient-specific 3D brain representation represents a cortical surface of the patient's brain and modifying the patient-specific 3D brain representation maintains size of a sub-cortical structure representation of the patient-specific 3D brain representation representing a sub-cortical structure of the patient's brain being targeted for surgery;

determining a level of safety for a prospective surgical trajectory based on a number of intersections between a prospective surgical trajectory representation representing the prospective surgical trajectory and an exterior boundary surface of the modified patient-specific 3D brain representation, wherein the determined level of safety increases with a decreasing number of times the prospective surgical trajectory representation intersects the exterior boundary surface of the modified patient-specific 3D brain representation, and wherein the exterior boundary surface of the modified patient-specific 3D brain representation comprises a safety margin-modified representation of the cortical surface of the patient's brain; and generating and displaying, on a graphical user interface (GUI), the prospective surgical trajectory representation overlaying a visual representation of the patient's brain with a visual indicator indicating the determined level of safety for the prospective surgical trajectory.

10. The non-transitory computer-readable media of claim 9, wherein the visual representation of the brain structure of the patient comprises at least one of:

the patient-specific 3D mesh cortical surface representation; or a scan of the patient's brain, wherein the imagining data comprises the scan.

11. The non-transitory computer-readable media of claim 9, wherein the visual indicator comprises color-coding for the prospective surgical trajectory representation that indicates the determined level of safety for the prospective surgical trajectory.

12. The non-transitory computer-readable media of claim 11, wherein the visual indicator comprises color-coding such that:

a first color version of the prospective surgical trajectory representation indicates a first level of safety;

a second color version of the prospective surgical trajectory representation indicates a second level of safety lower than the first level of safety; and a third color version of the prospective surgical trajectory representation indicates a third level of safety lower than the second level of safety.

13. The non-transitory computer-readable media of claim 9, wherein, the method further comprises:

using the imaging data of the patient's brain to generate a 3D hazard brain region representation representing a hazard brain region of the patient's brain to be avoided during surgery; and increasing the hazard brain region representation in size in accordance with the surgical safety margins.

14. The non-transitory computer-readable media of claim 13, wherein increasing the one or more 3D hazard brain region representations in size comprises, for a given 3D hazard region representation, applying a dilation filter to expand the given 3D hazard region representation voxel-wise.

15. The non-transitory computer-readable media of claim 13, wherein increasing the hazard brain region representation in size comprises, outwardly displacing individual voxels of a 3D boundary surface of the 3D hazard region representation by a set amount along surface normals of the individual voxels, the 3D boundary surface of the 3D hazard region representation representing the exterior boundary surface of the hazard brain region represented by the 3D hazard region representation.

16. A system comprising:

one or more processing resources; and non-transitory computer-readable media, coupled to the one or more processing resources, having stored therein instructions that when executed by the one or more processing resources cause the system to perform a method comprising:

adapting a generalized three-dimensional (3D) mesh brain representation to imaging data of a patient's brain to generate a patient-specific 3D mesh brain representation representing the patient's brain;

modifying the patient-specific 3D brain representation in accordance with surgical safety margins by at least one of:

applying an erosion filter to remove outermost voxels at an exterior boundary surface of the patient-specific 3D brain representation, or inwardly displacing individual voxels from the exterior boundary surface of the patient-specific 3D brain representation by a set amount along downwards projections from surface normals of the individual voxels, wherein the exterior boundary surface of the patient-specific 3D brain representation represents a cortical surface of the patient's brain and modifying the patient-specific 3D brain representation maintains size of a sub-cortical structure representation of the patient-specific 3D brain representation representing a sub-cortical structure of the patient's brain being targeted for surgery;

generating a bit mask from the modified patient-specific 3D brain representation;

generating a modified patient-specific 3D cortical surface representation representing a safety margin-modified cortical surface of the patient's brain by applying a marching cubes algorithm to the bit mask;

in response to user input that identifies a target point within the sub-cortical structure of the patient's brain and a prospective entry point for initially entering the patient's brain, generating a prospective surgical trajectory representation representing a prospective surgical trajectory that connects the prospective entry point and the target point;

determining a level of safety for the prospective surgical trajectory based on a number of times the prospective surgical trajectory representation intersects the modified patient-specific 3D cortical surface representation, wherein the determined level of safety increases with a decreasing number of times the prospective surgical trajectory representation intersects the modified patient-specific 3D cortical surface representation; and generating and displaying, on a graphical user interface (GUI), the prospective surgical trajectory representation overlaying a visual representation of the patient's brain with a visual indicator indicating the determined level of safety for the prospective surgical trajectory.

17. The system of claim 16, wherein:

the method further comprises generating a 3D hazard brain region representation using the imaging data of the patient's brain, the 3D hazard brain region representation representing hazard brain region to be avoided during surgery; and determining the level of safety for the prospective surgical trajectory further comprises determining the level of safety for the prospective surgical trajectory based on proximity of the prospective surgical trajectory representation to the 3D hazard brain region representation.

18. The system of claim 17, wherein determining the level of safety for the prospective surgical trajectory based on the proximity of the prospective surgical trajectory representation to the 3D hazard brain region representation comprises determining an extent to which the prospective surgical trajectory representation passes within a threshold distance to the 3D hazard brain region representation.

19. The system of claim 18, wherein determining the extent to which the prospective surgical trajectory representation passes within the threshold distance to the 3D hazard brain region representation comprises:

computing, for each individual point of the prospective surgical trajectory representation, distance to a 3D boundary surface of the 3D hazard brain region representation, the 3D boundary surface of the 3D hazard brain region representation representing an exterior boundary surface for the hazard brain region represented by the 3D hazard brain region representation; and determining a number of computed distances that are less than the threshold distance.

20. The system of claim 18, wherein:

the prospective surgical trajectory representation comprises a one-dimensional (1D) line; and the threshold distance is based in part on diameter of a surgical tool to be inserted into the patient's brain along the prospective surgical trajectory.

* * * * *